United States Patent [19]
Rapkin et al.

[11] Patent Number: 5,856,670
[45] Date of Patent: Jan. 5, 1999

[54] CONTINUOUS SAMPLE DETECTOR WITH MULTIPLE CELLS

[76] Inventors: Edward Rapkin, 180 White Oak Ridge Rd., Short Hills, N.J. 07078; Gavin A. Steele, 4101 Swann Ave., Tampa, Fla. 33609

[21] Appl. No.: 799,155

[22] Filed: Feb. 14, 1997

[51] Int. Cl.⁶ .................................................. G01T 1/204
[52] U.S. Cl. .................. 250/252.1; 250/364; 250/432 R
[58] Field of Search ............................... 250/336.1, 364, 250/432 R, 435, 252.1 R, 252.1 A, 437

[56] References Cited

U.S. PATENT DOCUMENTS

| | | |
|---|---|---|
| 3,188,468 | 6/1965 | Packard . |
| 3,381,130 | 4/1968 | Nather . |
| 3,560,744 | 2/1971 | Jordan . |
| 3,609,361 | 9/1971 | Shevick . |
| 3,723,736 | 3/1973 | Laney . |
| 3,724,956 | 4/1973 | Neary . |
| 3,935,449 | 1/1976 | Reunanen . |
| 4,027,163 | 5/1977 | Saito et al. . |
| 4,092,539 | 5/1978 | Pao et al. . |
| 4,107,533 | 8/1978 | Tabuchi et al. ........................ 250/364 |
| 4,194,117 | 3/1980 | Gross . |
| 4,292,520 | 9/1981 | Jordan . |
| 4,435,644 | 3/1984 | Heki ....................................... 250/435 |
| 4,495,420 | 1/1985 | Chudy et al. . |
| 4,528,450 | 7/1985 | Valenta . |
| 4,574,196 | 3/1986 | Kampf . |
| 4,634,869 | 1/1987 | Korobchenko et al. . |
| 4,791,820 | 12/1988 | Lawrence et al. . |
| 4,833,326 | 5/1989 | Valenta et al. . |
| 4,841,151 | 6/1989 | Shope . |
| 4,853,945 | 8/1989 | Rich et al. . |
| 4,893,934 | 1/1990 | Hansen . |
| 4,924,093 | 5/1990 | Johnson et al. . |
| 4,967,084 | 10/1990 | Rich et al. . |
| 4,982,096 | 1/1991 | Fujii et al. . |
| 5,146,093 | 9/1992 | Valenta et al. . |
| 5,166,526 | 11/1992 | Dietzel .................................. 250/435 |
| 5,285,071 | 2/1994 | LaCount ................................ 250/343 |
| 5,317,158 | 5/1994 | McElhaney et al. . |
| 5,328,662 | 7/1994 | Ringot et al. . |
| 5,334,536 | 8/1994 | Nonnenmacher . |
| 5,416,329 | 5/1995 | Sonne et al. . |
| 5,559,324 | 9/1996 | Rapkin et al. . |

FOREIGN PATENT DOCUMENTS

| | | |
|---|---|---|
| 0047049 | 3/1982 | European Pat. Off. . |
| 55-156881 | 12/1980 | Japan . |
| 56-8582 | 1/1981 | Japan . |
| 56-92484 | 7/1981 | Japan . |
| 61-53584 | 3/1986 | Japan . |
| 1231396 | 5/1971 | United Kingdom . |
| WO80/1609 | 8/1980 | WIPO . |

Primary Examiner—Constantine Hannaher
Assistant Examiner—Darren M. Jiron
Attorney, Agent, or Firm—Thomas L. Adams

[57] ABSTRACT

A continuous sample detector has a cell assembly with a spaced pair of sample cells. Each of these cells is mounted in a sample chamber and each is adapted to conduct a continuous sample flow. These sample cells are connected through a plurality of sample lines. The continuous sample detector also includes a sensor that is mounted and arranged proximate the cell assembly. Relative motion between the sensor and the cell assembly will enable the sensor to alternately detect radiation predominantly from a selected one of the cells. The sensor and the cells are positioned within the common housing to detect radiation with the sensor from predominantly a first one of the sample cells. The sample flow may at that time pass through the first one of the sample cells. The relative position of the sensor and the sample cells may then be changed within the common housing to detect radiation with the sensor from predominantly a second one of the sample cells. The sample flow may at this time pass through the second one of the sample cells, without disconnecting any of the plurality of sample lines.

48 Claims, 5 Drawing Sheets

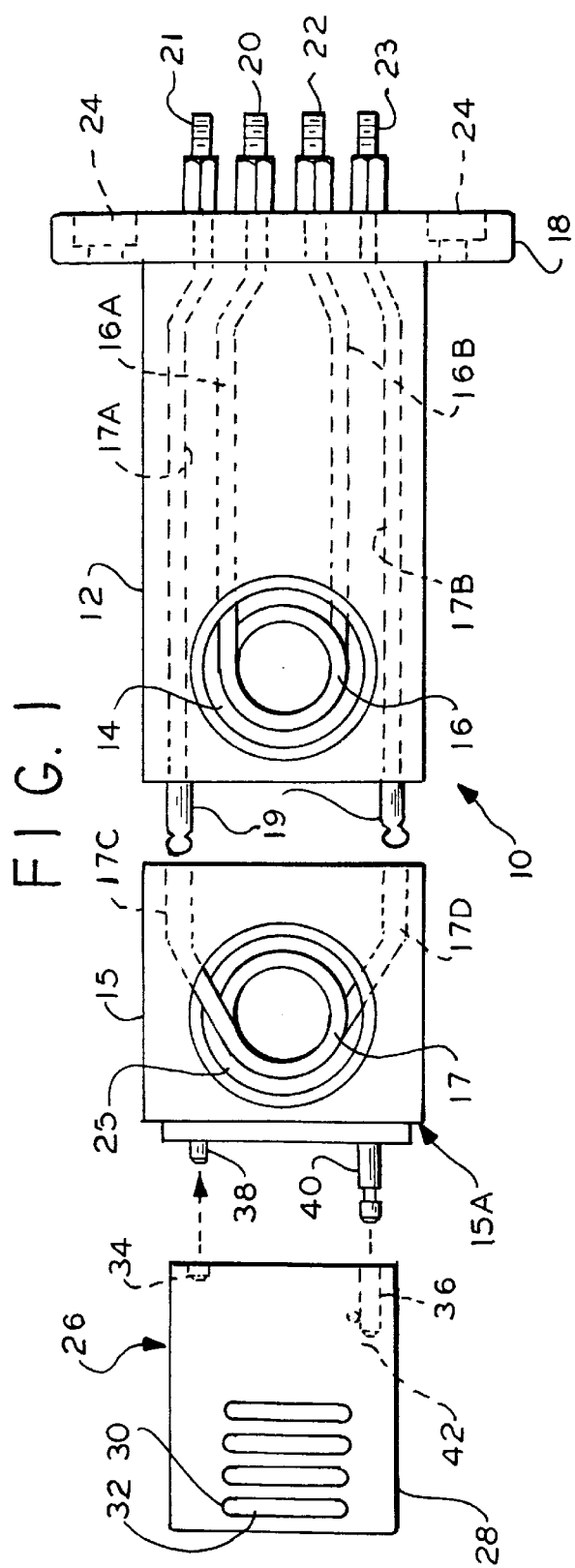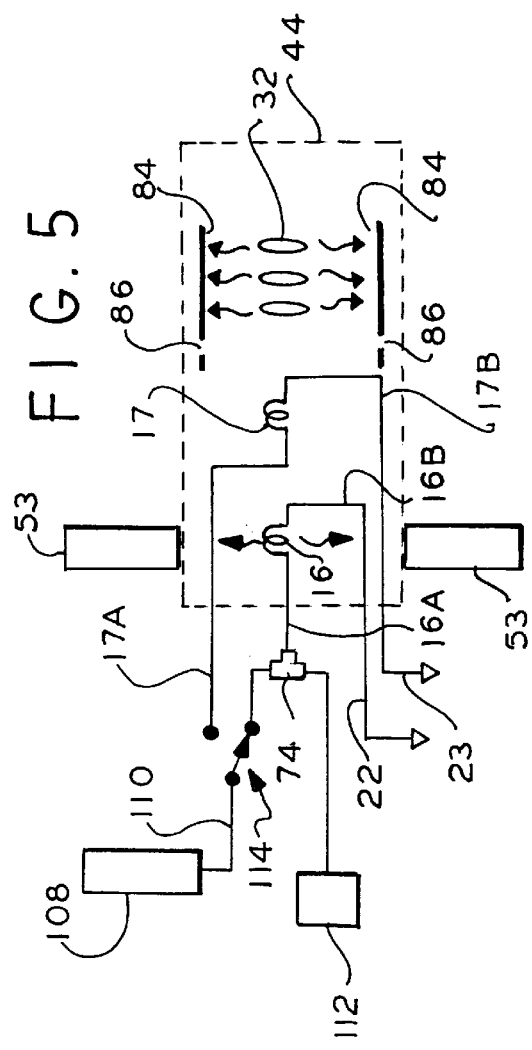

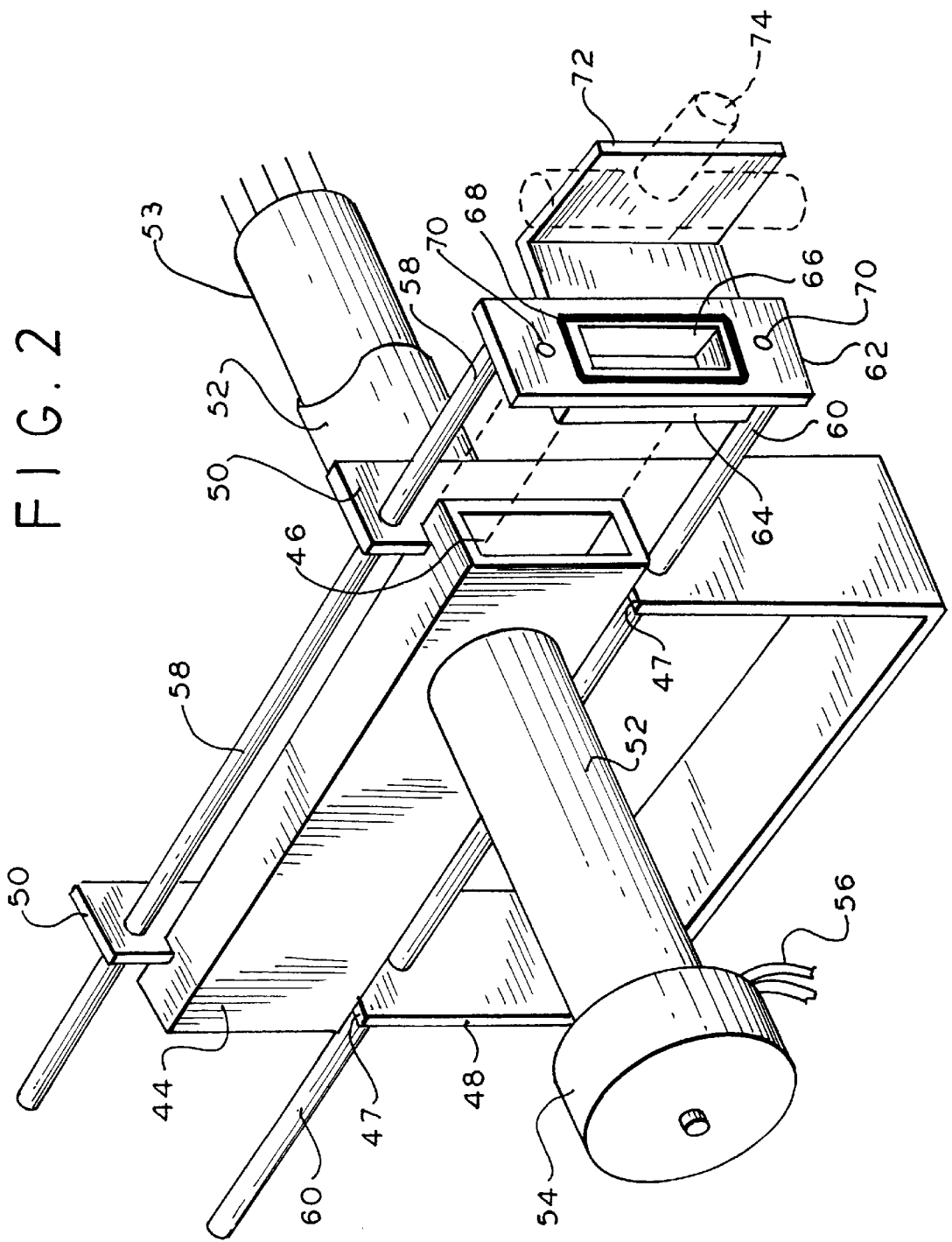

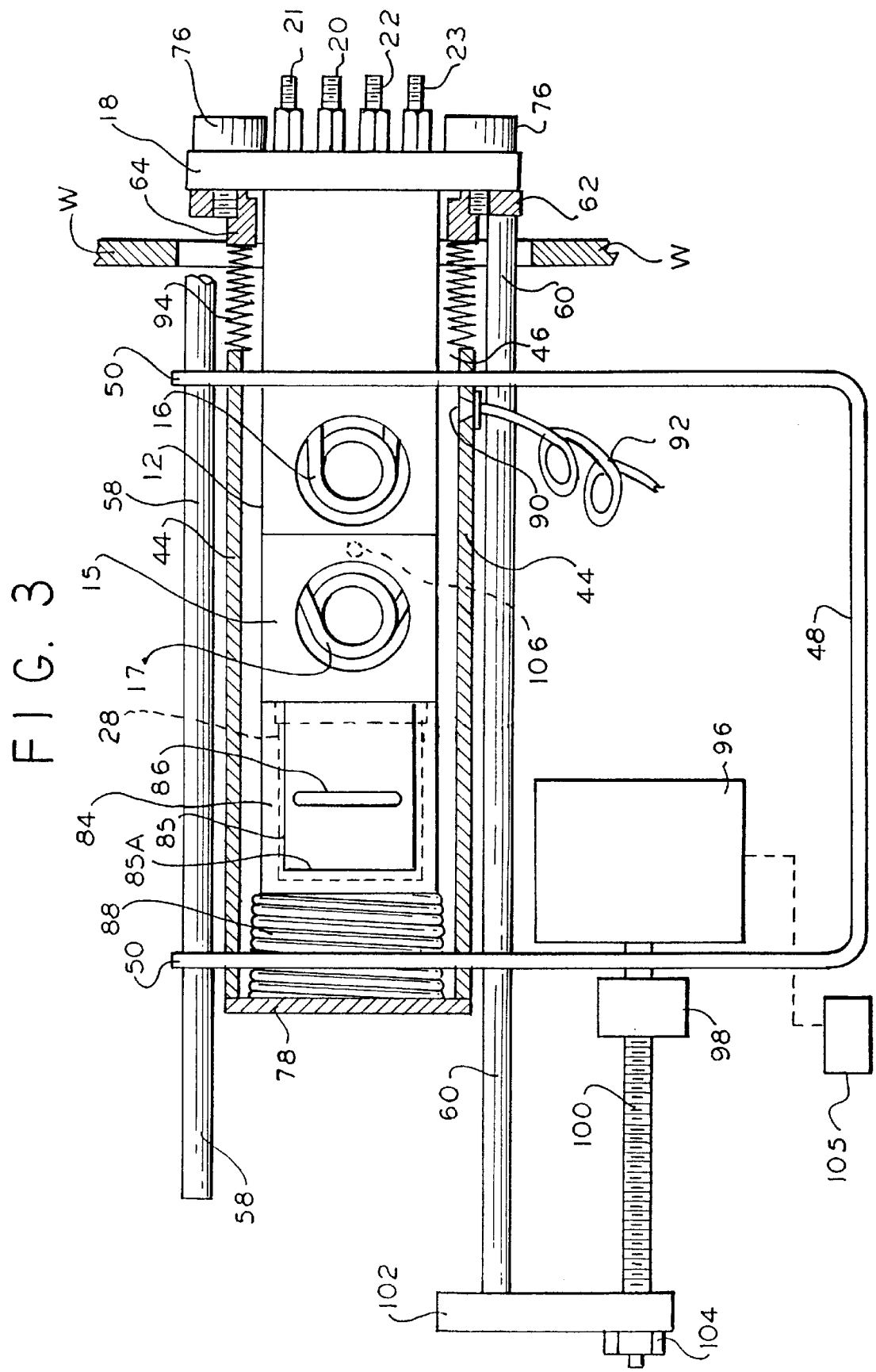

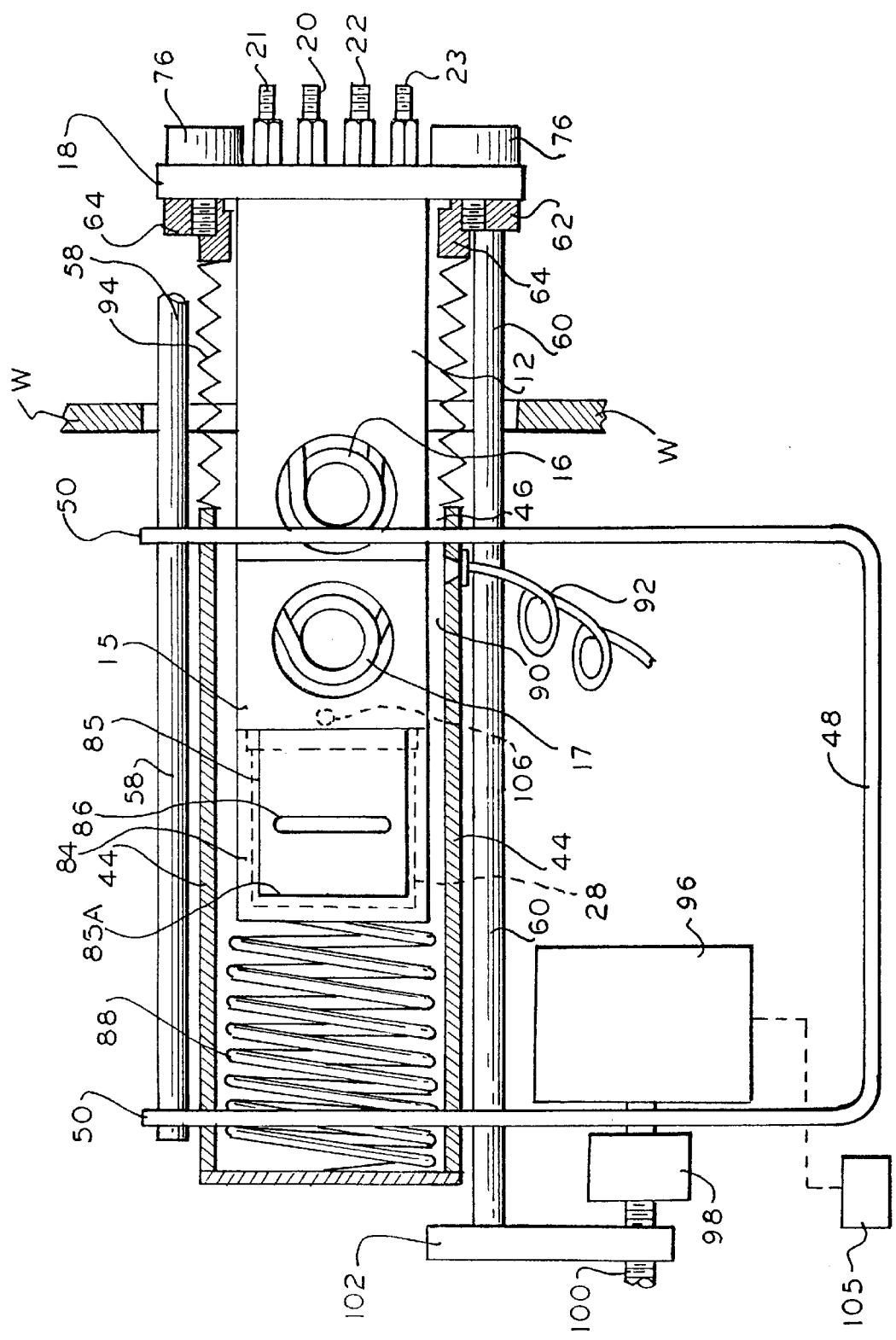

CONTINUOUS SAMPLE DETECTOR WITH MULTIPLE CELLS

BACKGROUND OF THE INVENTION

1. Field of the Invention

The present invention relates to continuous sample detection, and in particular, to the use of multiple cells for facilitating measurements.

2. Discussion of Related Art

The effects of a radioactive tracer introduced into an organism may in part be determined by removing tissue samples for analysis. A known method of detecting these radioactive tracers is to pass extracts, digests, and other solutions derived therefrom through a chromatography column to separate their constituents into various fractions, in the usual fashion. The eluate from the chromatography column can then be passed through a device for detecting the radioactivity.

Radioactivity detection is often practiced with a flow-through detector that continuously monitors the radiation from samples flowing through a cell. When the continuous flow to the cell is the eluate from a high performance liquid chromatography column (HPLC) large amounts of information can be obtained through numerical and graphical analysis.

In a known detection technique, the eluate is continuously mixed with a scintillating solution and passed through a transparent tubular cell mounted in a sample block inside a light-tight box. Alternatively, scintillation solution need not be used and instead, the eluate is passed over insoluble scintillator particles within the cell. The faint light coming from the tubular cell is detected by a pair of photomultiplier tubes on opposite sides of the cell. See for example, U.S. Pat. No. 4,194,117.

There are occasions when the type of cell ought to be changed in systems of the above type. For example, two technicians might be sharing one detector system and each could require or prefer a different sample cell configuration. In that case, each technician would need to replace the sample cell before beginning test operations. Also, cell changes may be desirable when technicians use the detector with automatic sample injectors which can have a capacity of a hundred samples or more. Different batches of samples (or simply different preferences) may indicate the need for a different sample cell. In such an automated system, there is no provision for dealing automatically with changed requirements when proceeding to a new batch. Operators have therefore, settled with a compromise cell that is not ideally tailored to either batch.

Any attempt to run large batches can be frustrated if successive batches require a different sample cell and a compromise cell is unsatisfactory. In such situations, the batches cannot be run automatically, but the process must stop so that an operator can intervene and change the sample cell.

Another area of unfortunate compromise results from the fact that the amount of radiation from a sample will change over time as different fractions are delivered in the eluate from a chromatography column. It is difficult to choose a sample cell that will work adequately for low activity peaks as well as high activity peaks occurring in one sample. Low activity peaks can be more easily measured with larger cell volumes that have greater sensitivity. On the other hand, with large cell volumes and increased counting time, it is possible to overwhelm the electronics with excessive numbers of counts. Also the larger cell volumes have less resolution and may not be able to distinguish between closely spaced peaks. Accordingly, operators will try to strike a balance between these competing requirements.

Changing from one flow-cell to another flow-cell is difficult. In most instruments, the cover must be removed, the high voltage disabled, plumbing fittings disconnected, the cell removed (potentially causing problems with ambient light as explained below), the new cell installed, the cover replaced, and the high voltage reestablished. Finally, the measurement can be made. To later return to the original cell, all of the forgoing steps must be repeated.

The high voltage must be turned off each time a cell is removed or inserted. Exposure of a photomultiplier to ambient light with the high voltage applied can cause irreparable damage, since the consequential high current flows will likely "strip" the photocathodes.

Regardless, removing the high voltage is inherently problematical, because photomultipliers are most quiet (i.e., least electronic noise) when kept at constant high voltage for long periods. Similarly, even with the high voltage off, exposure to ambient light can cause photocathodes to become light activated, requiring then a lengthy period of dark adaptation to reduce background noise to minimum levels.

Similarly, removal and ambient illumination of cells packed with solid scintillators (particularly the popular yttrium silicate) cause phosphorescence, again requiring a lengthy period of dark adaptation before the cell reaches its lowest backgrounds.

Furthermore, repetitively disconnecting and reconnecting fittings is an invitation to leaks, especially at the high pressures that are apt to be encountered in HPLC. Cleanup of leakage of radioactive solutions may have heavy consequences.

External standardization has been used in liquid scintillation systems to determine the quality of individual samples, especially for quenching phenomena. With that technique, an external radioactive source is brought near the sample to determine how the scintillation process varies in response to known radioactive stimulation. See for example, U.S. Pat. Nos. 3,609,361; 3,188,468; and 3,381,130. For other quenching correction techniques, see U.S. Pat. Nos. 4,008,393 and 4,292,520. See also U.S. Pat. Nos. 3,935,449 and 4,967,048.

In U.S. Pat. No. 5,559,324 standardization is performed on a continuous flow, radiochromatography system. That disclosed device has a sample holder mounted on an axially movable block. A standard holder is mounted on the rear of the cell block. Accordingly, the sample cell and standards can be moved to place either one in the proximity of a photomultiplier tube. Thus, the system can be calibrated, for example, with a sealed standard without the need to disconnect the sample cell from the sample lines. This reference teaches the advantage of avoiding exposing the photomultiplier to ambient light and avoiding the inconvenience of disconnecting and reconnecting plumbing to the sample cell. The reference, however, does not teach the importance of quickly changing flow sample cells.

In U.S. Pat. No. 4,853,945 multiple cells are used simultaneously, not sequentially. FIG. 5 shows eluate from a chromatography column flowing past six (6) stations. Each of these stations are connected by light pipes to separate photomultipliers. While there are effectively different stations at which measurements are made, this system has the disadvantage of requiring simultaneous measurement. The system is designed to increase the effectiveness of the photomultipliers by monitoring six (6) stations with four (4) tubes. The origin of pulses is determined by correlating the pulses. Furthermore, systems relying on correlation do not operate accurately, because accidental coincidences occur once the true count rate in one sample or cell becomes greatly elevated, as is often the case. Even if there are no true counts in other samples or cells being examined at the same time, there will be a high rate of accidental coincidences arising from these photomultiplier pairs that involve the hot sample and the others.

The nature of these false coincidences can be also understood by referring to U.S. Pat. No. 3,723,736 which shows a trio of equiangularly spaced photomultiplier tubes. Each of three samples is positioned among the photomultiplier tubes to straddle and shine upon a pair of the tubes. Assume a first sample has a very high count rate, a second sample has nothing, and the third sample has some modest count rate. The coincidence rate from the photomultiplier pair illuminated by the very high count rate will likely give a reasonably accurate result for the high count rate. Still, one member of this highly stimulated pair, however, will also be correlated with the remaining tube to determine the count rate for the inactive sample. There will be accidental coincidences for the pair covering the inactive sample, since one of the pair is highly stimulated (plus noise) and the other will be modestly stimulated but not by the inactive sample. Thus, the inactive sample will seem to have correlated counts from its two tubes although they will be derived mostly from accidental correlation between the other two samples (plus noise), one of which is highly active. Further, if any of these samples should have luminescence problems, a common occurrence, there will be some effect on the other samples.

The accidental coincidence rate of two (2) random noise generators is a function of $n_1$, $n_2$, and T, where $n_1$ and $n_2$ are the non-coincident count rates of each tube and T is the coincidence resolving time of the circuit. Because a product is involved, when either count rate goes up substantially, the accidental rate climbs correspondingly. One might conclude that this could be made negligible with faster coincidence circuitry, but an unfortunate characteristic of photomultipliers is that transit time (the time from propagation of a pulse at the photocathode until it can be sensed at the anode) is rather variable. If the coincidence time is made too short, true coincidences are missed and the counting efficiency goes down. U.S. Pat. No. 4,853,945 acknowledges this problem (column 4, lines 18, et seq.).

Another disadvantage with systems of this type is that as the sample moves along through the various cells, it is measured by four (4) different pairs of photomultipliers, each possibly having slightly different responses. Since the different cells will be in principle working together and simultaneously, it is unclear that such a system would work properly if the cells had different characteristics.

Another system shown in U.S. Pat. No. 4,027,163 shows a pair of serially connected radioactivity detectors. The downstream detector also has a standard radioactive source. This reference is designed to collect data from the two (2) collectors simultaneously and, therefore, is not designed to avoid the expense of having multiple detectors for multiple sites. U.S. Pat. Nos. 4,924,093 and 5,416,329 show detection of radiation from discrete samples, that is, vials. These references are unconcerned with systems for monitoring radiation from a flowing sample.

See also U.S. Pat. Nos. 4,791,820; 4,495,420; 4,528,450; and 5,328,662.

Accordingly, there is a need for an improved, continuous sample detector that provides the benefit of the specialized characteristics offered by different types of sample cells, but without multiplying the time or the amount of sensors needed to achieve such flexibility and adaptability.

SUMMARY OF THE INVENTION

In accordance with the illustrative embodiments demonstrating features and advantages of the present invention, there is provided a continuous sample detector. This detector has a sample chamber and a cell assembly with a spaced pair of sample cells. Each of these cells is mounted in the sample chamber and each is adapted to conduct a continuous sample flow. The continuous sample detector also includes a sensor that is mounted and arranged proximate the cell assembly. Also included is a motion means for allowing relative motion between the sensor and the cell assembly to enable the sensor to alternately detect radiance predominantly from a selected one of the cells.

In accordance with another aspect of the invention, a method employs a sensor for continuously detecting in a sample flow, radiance predominantly from one of a pair of sample cells within a common housing. These sample cells are connected through a plurality of sample lines in a cell assembly. The method includes the step of positioning the sensor and the cells within the common housing to detect radiance with the sensor from predominantly a first one of the sample cells. Another step is passing the sample flow through the first one of the sample cells. The method also includes the step of changing the relative position of the sensor and the sample cells within the common housing to detect radiance with the sensor from predominantly a second one of the sample cells. Another step is passing the sample flow through the second one of the sample cells, without disconnecting any of the plurality of sample lines.

Reference herein to "radiance" shall include such phenomena as light, radioactivity, electromagnetic radiation, particle emission, etc.

Preferred apparatus and methods according to the foregoing principles may employ a main cell body supported on a faceplate and slidably mounted inside a dark sample chamber. Fittings on the faceplate connect preferably to a sample cell in the main cell body. Other fittings on the faceplate connect to sample lines that lead to preferred couplings on the inside end of the main cell body. These couplings allow a second sample cell to be mounted behind the main cell body while still being supplied by fittings on the faceplate. Thus, the preferred faceplate can service two sample cells that are spaced one behind the other. In some embodiments, more than two sample cells may be employed.

By mounting multiple, spaced sample cells inside the sample chamber, the operator can easily select a desired one of the sample cells. In a preferred embodiment, the cell assembly can be slid linearly to place a selected one of the sample cells between a pair of photomultiplier tubes.

An optional standard can be mounted behind the two sample cells and can employ a plurality of spaced, sealed standards. These standards can be used to calibrate a photomultiplier in accordance with the principles disclosed in U.S. Pat. No. 5,559,324. A standard holder mounted at the inside end of the inside sample block, may have has several slots holding sealed standards for calibrating the system. The sample blocks and the standard holder can be shifted axially to displace the continuous sample cells and bring one of the sealed standards in alignment with the photomultiplier tubes. This motion preferably brings a shutter into play so that only one of the sealed standards shines on the photomultiplier tubes at a time.

The combination can readily slide as an assembly into various working positions. The motion is modest and therefore the lines to the sample cell need not be disconnected. Also, motion of the sample blocks can be performed in darkness in a light-tight sample chamber. Any gap between the light-tight chamber sample block can be shielded for example, by a preferred, light-tight bellows.

In the preferred embodiment, multiple sample cells are used that each have different characteristics tailored to different samples. Thus, an operator can quickly change sample cells to accommodate various samples that may be supplied from a chromatography column. For example, some samples may exhibit closely spaced, high activity peaks and would be best measured by a relatively small cell volume having high resolution. On the other hand, measurement of low activity peaks would be best accomplished by a larger cell volume having longer residence times and enhanced sensitivity.

Also, the multiple cells can have different characteristics that are tailored to various types of radiance. For example, one of the cells may be best adapted to detect beta radiation, while another cell may be adapted to detect soft gamma radiation. Moreover, one or more of the cells may be adapted to detect Cerenkov radiation. Furthermore, a variety of scintillation techniques can be offered, where one cell may employ a solid scintillator, while another cell can operate with liquid scintillators that are injected through lines connecting to this other cell.

In some cases the cells will be alternately connected to a source of eluate by means of a switching valve. In other embodiments, the sample cells can be connected in series to eliminate the need for valves. With a series connection, the smaller cell would most likely be in the upstream position, so that resolution is best preserved. While such a system would eliminate the need for a valve, it would increase the back pressure on the system. Another potential drawback to series connections occurs when the samples contain substances that adhere to one scintillator but not to the other. In that case, a valve would be preferred to a series connection.

In highly preferred embodiments, the cells can be repositioned by means of a stepper motor that operates a lead screw to linearly move the cell assembly. The stepper motor and lead screw can reciprocate a plate that supports the cell assembly in order to substitute one of the sample cells for another at the photomultiplier tubes.

Also, such movement of the cell assembly can be automatically scheduled by a computer running a scheduling program. Changing cells automatically between runs is highly convenient when an operator is present, but can also be an important way to increase equipment utilization for overnight or weekend tests, when no attendant is present.

In some embodiments cell changes can be programmed to occur during a single HPLC run. This feature provides enhanced performance hitherto impossible. Thus, the cell can be changed "on the fly" to accommodate a large active peak that requires a relatively small cell. Afterwards, the cell can be replaced with a larger cell to increase sensitivity.

BRIEF DESCRIPTION OF THE DRAWINGS

The above brief description as well as other objects, features and advantages of the present invention will be more fully appreciated by reference to the following detailed description of presently preferred but nonetheless illustrative embodiments, in accordance with the present invention, when taken in conjunction with the accompanying drawings, wherein:

FIG. 1 is an exploded, side elevational view of a cell assembly and optional standard holder, in accordance with principles of the present invention;

FIG. 2 is an axonometric view of a sample chamber with a sensor mounted thereto and suitable for receiving the cell assembly and optional standard holder of FIG. 1;

FIG. 3 is a side elevational view, partly in section, of the sample chamber of FIG. 2 with the cell assembly and optional standard holder of FIG. 1 installed;

FIG. 4 is a side elevational view of the apparatus of FIG. 3, but with the faceplate extended by the illustrated drive mechanism; FIG. 5 is a schematic illustration of the apparatus of FIGS. 3 and 4 shown hydraulically connected to a sampling system;

and

Figure 6A:
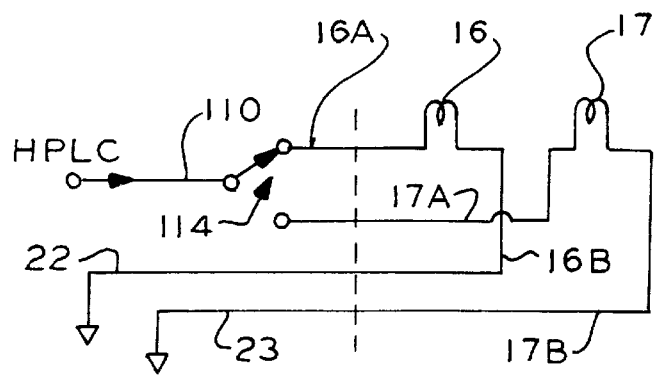
FIG. 6A is a schematic illustration of switchable hydraulic connections that are an alternate to the connections shown in FIG. 5.
Figure 6B:
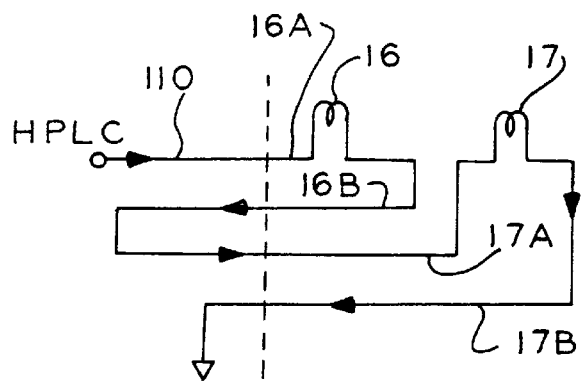
FIG. 6B is a schematic illustration of serial hydraulic connections that are an alternate to the connections shown in FIG. 5.
Figure 6C:
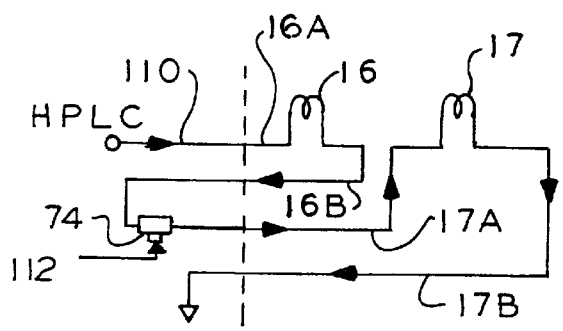
FIG. 6C is a schematic illustration of an alternate system that adds downstream injection of liquid scintillator to the sampling system of FIG. 6B.
Figure 6D:
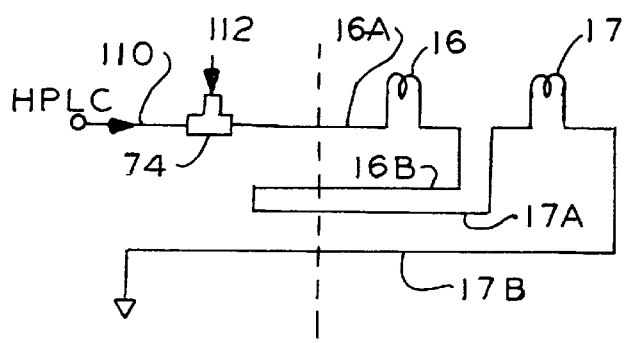

FIG. 6D is a schematic illustration of an alternate system that adds upstream injection of liquid scintillator to the sampling system of FIG. 6B.

DETAILED DESCRIPTION OF PREFERRED EMBODIMENTS

Referring to FIG. 1, cell assembly 10 has a rectangular block 12 made of machined steel or aluminum, although plastics, ceramics or other materials can be used instead. Fitted in a transverse circular opening 14 at the inside end of cell block 12 is a sample cell 16, shown in the form of a coil of optically transparent, $\frac{1}{16}$ inch (1.6 mm) chromatography tubing made of Teflon™ (synthetic resin). While two turns are illustrated, in other embodiments a different number of turns may be used instead. The void volume of the cell is typically from 200 to 1,000 microliters, but for some applications volumes in the range of 10 to 2,500 microliters are contemplated.

Tubing 16 extends in bores in cell block 12 along an inlet branch 16A and along an outlet branch 16B. Tubing branches 16A and 16B fit through corresponding apertures in front faceplate 18 to couple to inlet fitting 20 and outlet fitting 22, respectively. Faceplate 18 has a pair of countersunk bores 24 used to attach cell assembly 10 to structure described presently.

An additional pair of fittings 21 and 23 connect to sample lines 17A and 17B, respectively. Sample lines 17A and 17B are installed in longitudinal channels that are milled in the upper and lower edges of cell block 12. Lines 17A and 17B may be formed of tubing of the same type as lines 16A and 16B.

The distal, inside ends of lines 17A and 17B connect to a pair of couplings 19. Couplings 19 are in the form of plugs that can snap into sockets 17C and 17D in a second cell block 15, which is also part of the cell assembly 10.

Sockets 17C and 17D connect to tubing 17, made preferably of Teflon™ (synthetic resin). Tubing 17 may be formed similarly to sample tubing 16, although each may have different volumes for the reasons noted above. Tubing 17 is formed into a coil having two turns and acting as a sample cell. This sample cell is shown centrally mounted in a circular opening 25 in cell block 15.

Ideally, couplings 19 are quick-disconnect fittings that allow an operator to quickly replace the second cell block 15. Nevertheless, quick-disconnect couplings may, in some cases, be unable to adequately handle the relatively high pressure associated with HPLC. In those cases, conventional pressure fittings may be employed to connect to the cell block 15. Such fittings may use ferrules that are tightened to deform and swage into the tubing associated with the cell 17. When the second cell 17 is connected with these more conventional fittings, cell 17 is not readily disconnected from the system and normally the entire cell assembly would be removed and returned to the factory where a different combination of cells can be assembled. In some embodiments, the tubing associated with cell 17 will run continuously from the opening 25 to the fittings 21 and 23, so there is no intermediate joint, only a joint at the fittings 21 and 23.

The transverse dimensions of cell block 15 (height and thickness) are shown about the same as block 12, but need not be so. In some embodiments block 12 may be bigger or smaller. In any event, block thickness should be kept small to minimize separation of the photomultiplier tubes. The inside end of block 15 is milled to have a step 15A, which reduces the transverse dimensions by about 1/16 inch (1.6 mm). As described further hereinafter, step 15A allows the inside end of block 15 to fit into the shutter described hereinafter.

Cells 16 and 17 are used to detect radiation. As explained hereinafter, a mixture of a sample and a scintillating fluid can pass through tubing 16 and/or tubing 17. Radioactivity in the sample can stimulate the scintillating fluid to generate photons, which can be detected by the sensor described presently. Alternatively, the tubular cells 16 and/or 17 can be packed with a solid material that scintillates in response to radioactivity in the sample, thereby obviating the need for liquid scintillators. Among known packing materials are yttrium silicate, and calcium fluoride, and scintillating glass.

In some embodiments, sample cells 16 and 17 may have different characteristics, each adapted to respond best to different forms of radiation.

For example, one sample cell may respond best to beta radiation, while the other responds best to soft gamma radiation.

For soft gamma radiation such as I-125 and Tc-99m, one can employ cells that are made by sandwiching a Teflon™ (synthetic resin) coil, almost identical to those used in liquid scintillator cells, between two thin disks of scintillating material. In one preferred embodiment this scintillating material is thallium-activated sodium iodide. The gamma radiation is sufficiently energetic to pass out of the coil and into the scintillating material to produce light.

Most often, the two cell types (beta and gamma) would be used independently, although it is possible to develop mixtures of beta- and soft gamma-emitters, so that on a preprogrammed basis, and within one HPLC run, one cell or the other would be in place for a part of each measurement. In some embodiments a Cerenkov cell may be used and may be deemed a specialized form of liquid scintillator cell, except that scintillator solution is not added.

An optional standard source of radiation 26 is shown herein as a rectangular holder block 28 having four slots 30 containing sealed standards 32. Source 26 may be fabricated in accordance with the disclosure of U.S. Pat. No. 5,559,324. Standards 32 may be sealed glass vials containing a scintillating solution mixed with a radioactive isotope. Thus the self-contained radioactive isotope stimulates the scintillating solution to produce a faint light, simulating the type of light produced during a normal sample test.

Four sealed standards, 32 are illustrated. Each may have a different light intensity or a different scintillating fluid or isotope. Thus by selecting different ones of the standards 32, the photon flux can be varied to allow calibration of the system under various standard conditions.

Standard block 28 has a short blind bore 34 and a longer blind bore 36 sized to hold prongs 38 and 40, which project from the inside end of cell block 15. Mounted transversely and adjacent to bore 36 is a spring loaded ball 42 designed to engage the annular groove encircling the tip of prong 40. Thus prong 40 is fixed into position inside standard block 28 by ball 42.

Referring to FIG. 2, a light-tight (radiance-tight) sample chamber is shown as an elongate box 44, which is closed on five sides but open at end 46. The illustrated side walls of chamber 44 may be formed of a metal or plastic extrusion, although other materials may be used instead. Chamber 44 is shown resting atop shoulders 47 in U-shaped bracket 48. Bracket 48 is a metal strip having two vertical branches that terminate in upper projections 50, which have an inverted L-shape, sized to fit partially around the periphery of chamber 44.

Mounted on opposite sides of chamber 44 are a pair of support tubes 52, each containing a sensor in the form of a light sensitive transducer such as a photomultiplier tube. The support tubes are brazed or silver-soldered, to permanently affix them in place at openings (not shown) in chamber 44. The ends of tubes 52 are covered with a cap 54. A connection to the internal photomultiplier tubes 53 is made through wire leads 56. Conventional photomultipliers are preferred, although other sensors, such as phototransistor arrays, or other solid-state devices might be used instead. Moreover, in some embodiments radioactivity may be detected directly without employing a scintillating fluid or scintillating packing. In Cerenkov counting, light is directly generated by the passage of energetic beta particles from the sample substances through the fluid medium carrying them from the chromatography column.

Cylindrical, stainless steel rods 58 and 60 are slidably mounted in apertures in the upper ends of bracket 48. Rods 58 and 60 can be fitted into nylon bearings (not shown) in bracket 48. Specifically, rod 58 is mounted in the upper end of portion 50 of bracket 48 above one of the upper corners of chamber 44. Near the diagonally opposite corner of chamber 44 rod 60 is slidably mounted in bracket 48.

Mounted to the front ends of rods 58 and 60 is a yoke plate 62. Yoke plate 62 has a rectangular opening 66 matching opening 46 in chamber 44. Yoke plate 62 is a rectangular, annular, metal slab having a rear, annular embossment 64. Opening 66 is encircled by an annular groove containing an O-ring 68, used for the light sealing purposes described presently. Also, a pair of threaded holes 70 above and below opening 66 are used for securing a cell assembly to yoke plate 62 as also described presently.

Attached to an edge of yoke plate 62 is an L-shaped bracket 72 used to support a plumbing tee 74, shown herein in phantom. Instead of a separate bracket 72, in some embodiments one edge of yoke plate 62 can be extended to provide a mounting surface for the plumbing tee 74. Plumbing tee 74 is herein referred to as a mixing means having a first and second inlet. Because tee 74 is mounted to move with the cell body attached to yoke plate 62, a rigid tube can be used from the tee outlet to an inlet of the cell assembly.

Referring to FIG. 3, the previously mentioned faceplate 18 is shown attached to yoke plate 62 by means of thumb screws 76. Consequently, cell blocks 12 and 15 are shown attached together to support sample cells 16 and 17, respectively. Cell blocks 12 and 15, and optional standard block 28 are shown inside sample chamber 44, which is closed at its inside end with a cover plate 78. In this embodiment the stepped inside end of block 15 is shown fitting into the shutter 84. Shutter 84 may be a rectangular, U-shaped device having a rear face engaging spring 88 and two opposing faces with apertures 86 sized to match the outline of the individual standard slots 30. While shutter 84 is made from a block that is somewhat thicker than cell blocks 12 and 15, the faces of shutter 84 bearing apertures 86 are milled longitudinally to have relieved channels 85. This reduces the thickness of shutter 84 adjacent the photomultiplier tubes (tubes 53, FIG. 2). This reduced thickness increases clearance and avoids rubbing against the faces of the photomultipliers, even if closely spaced.

A rectangular spring 88 is mounted inside sample chamber 44 between the back plate 78 and the shutter 84. Spring 88 will normally keep shutter 84 in the illustrated position to cover the sealed standards described herein. As the cell assembly moves out, spring 88 can drive shutter 84 forward until the rear edge 85A of channel 85 reaches the shutter stops 106. The shutter stops 106 are a pair of set screws threaded through opposite sides of chamber 44. When stops 106 engage channel edge 85A the shutter opening 86 will be centered at the photomultiplier tubes to mask the sealed standards, except for any one standard that may be in registry with the shutter opening 86. The sealed standards are able to successively move into registry with the shutter opening 86 as the cell assembly moves.

Clearance at the bottom of sample chamber 44 below cell blocks 12 and 15 allows leakage, if any, to accumulate and flow through a drain 90. The drain 90 is shown in the floor of sample chamber 44 in the form of a hole near the opening 46 of chamber 44. Hole 90 is connected to spirally curled, opaque tubing 92 that can be led to an appropriate capture basin (not shown). The curls in tubing 92 act as a light trap to prevent light leakage into chamber 44.

Chamber 44 is arranged to be light-tight. A sleeve in the form of bellows 94 is cemented in place to encircle opening 46 of chamber 44. The forward end of bellows 94 is also cemented in place to encircle embossment 64 of yoke plate 62. As noted before, the O-ring on the front face of yoke plate 62 acts as a seal to plate 18. As thus arranged, sample chamber 44 is light-tight. Light can be introduced into the chamber only by either cells 16, 17 or sealed standards 32.

The assembly of FIGS. 3 and 4 is mounted inside a casing having a front wall W. The casing of wall W need not be light-tight but will produce a darkened interior for reducing stray illumination. The opening in wall W is sized to allow free passage of bellows 94 and rods 58, 60.

A motor means is shown herein as stepper motor 96 connected through coupler 98 to lead screw 100. Lead screw 100 is threaded into drive arm 102. When threaded lead screw 100 is spun by stepper motor 96, drive arm 102 rides on lead screw 100 in the manner of a nut on a lead screw. Secured to the outer end of lead screw 100 is a stop 104, which limits the extent of travel possible by drive arm 102. Consequently, drive arm 102 can axially reciprocate slider bar 60. As a result, bar 60, yoke plate 62, and slider bar 58 can slide together as a unit.

Motor 96 is connected to a controller 105. In simplified embodiments, controller 105 can be a manual switch to increment stepper motor 96. Alternatively, controller 105 can be a computerized unit, programmed to energize motor 96 in a sequence designed to accomplish the process hereinafter described.

Also in some embodiments, the cell blocks 12 and 15, as well as standard holder 28 (FIG. 1), can be repositioned manually and held in each position by mechanical detents that allow the operator to feel when the cells or sealed standards are in proper position. Also, while the cell blocks 12 and 15 are shown mounted next to each other, in other embodiments they may be spaced apart. Moreover, while axial reciprocation is used to swap the cell blocks 12 and 15 (or the sealed standards), in other arrangements the motion may be orbital and the cells and sealed standards may progress in a carousel-like motion. Also, while the cells and sealed standards are shown mobile, in other embodiments the photomultiplier tube itself may move among the cells and the sealed standards.

FIG. 5 schematically illustrates an experimental set up. Here a high pressure chromatography column 108 has an eluate output 110 connecting to a switchable inlet of two-way valve 114 (also referred to as a switching means). The high pressure chromatograph can operate in the range of 3,000 to 5,000 psi, although downstream pressure drops occurring prior to valve 114 bring the pressure at the valve and sample chambers closer to ambient. One outlet of valve 114 connects along line 17A to sample cell 17. The other outlet of valve 114 connects to one inlet of mixing tee 74 (also referred to as a mixing means), whose other inlet connects to a source 112 of liquid scintillator. The outlet of mixing tee 74 connects along previously mentioned line 16A to the inlet of previously mentioned cell 16, whose outlet connects along previously mentioned line 16B, through fitting 22, and to waste. Also, outlet line 17B of cell 17 connects through fitting 23 to waste.

A pair of photomultiplier tubes 53 is shown mounted in spaced opposing positions across the sample chamber 44. As described hereinafter, cells 16 and 17 can be alternately positioned between the photomultiplier tubes 53, unless sealed standards 32 are positioned between the photomultiplier tubes.

Referring to FIG. 6A, sample cells 16 and 17 are shown connected in the same manner as was shown in FIG. 5, except for the elimination of the mixing tee (tee 74 of FIG. 5). Therefore, inlet line 17A of sample cell 17 connects directly to one of the outlets of switching valve 114.

Referring to FIG. 6B, sample cells 16 and 17 are shown serially connected. Specifically, eluate can flow from source 110 along line 16A and through sample cell 16, before flowing through lines 16B and 17A to sample cell 17. Thereafter, the outlet of sample cell 17 flows along line 17B to waste.

In FIG. 6C, the cells 16 and 17 are again connected in series in a manner similar to that shown in FIG. 6B, except for the addition of mixing tee 74. Specifically, outlet line 16B connects to one inlet of mixing tee 74, whose other inlet connects to the previously mentioned source 112 of liquid scintillator. The outlet of mixing tee 74 connects to the inlet line 17A of sample cell 17, whose outlet is connected as before.

Referring to FIG. 6D, the sample cells 16 and 17 are again connected in series in a manner similar to that shown in FIG.

6B, except that inlet line 16A of cell 16 connects to the outlet of mixing tee 74. The two inlets of mixing tee 74 are shown separately connecting to the source of eluate 110 and the source of liquid scintillator 112.

When in the foregoing embodiments the two cells 16 and 17 are connected in series, the smaller cell would be in the upstream position. In a series connection employing a liquid scintillator cell, a Cerenkov cell would come first followed by a mixing tee, and then the second liquid cell. If the Cerenkov cell is used together with a packed cell, the Cerenkov cell would preferably take the upstream position.

Embodiments employing liquid scintillator cells having different volumes would often be connected in series with the smaller cell first. With that order, only one mixing tee would be needed, and no switching valve. If a gamma cell were used together with a liquid scintillator cell, the gamma cell would normally be positioned upstream with the liquid scintillator cell downstream. Liquid scintillator might be mixed with eluate before passing into a gamma cell, and should have no significant effect on performance, as long as corrections are made for added scintillator volume.

In embodiments employing a packed cell and a liquid cell, both might be independent and employ a switching valve, although a serial connection is also possible. In the serial case, the sample solution must first pass through the packed cell and then flow into a mixing tee where a liquid scintillator is added before flowing through the liquid cell. In embodiments where the cells comprise a packed cell and a soft gamma cell, the smaller cell would take the upstream position.

To facilitate an understanding of the principles associated with the foregoing apparatus, its operation will now be briefly described. The following assumes the configuration of FIG. 5, but similar remarks will apply to the configurations of FIGS. 6A–6D.

A normal test may be performed first with sample cell 16 active and oriented as shown in FIGS. 3 and 5. This cell position is achieved by commanding motor 96 through controller 105 to spin threaded lead screw 100 and drive arm 102 against stop 104. This draws rod 60 and 58 backward to the maximum extent to collapse the bellows 94. Plate 62 is thus retracted to bring cell block 12 to the illustrated position so cell 16 is aligned with the photomultiplier tubes 53. At this time, the sample cell 17 and sealed standards 32 are retracted enough so that effectively only radiance from cell 16 will reach the photomultiplier tubes 53.

When high pressure chromatography column 108 is started, the eluate output 110 feeds through valve 114 to one input of mixing tee 74, whose other input is fed scintillating fluid from the source 112. The output of mixing tee 74 feeds cell 16.

Different fractions of the eluate are separated by the chromatography column 108 in the usual fashion. In some instances a radioactive tracer may have been absorbed by tissues, extracts of which, after suitable treatment, can be analyzed in the chromatography column. Based on the separation characteristics of the chromatography column, the radioactive constituents reach mixing tee 74 at specific times relating to the chromatographic separation characteristics. In any event, the eluate sample is mixed with the scintillation fluid in the mixing tee 74 and delivered to cell 16.

In a known fashion, radioactivity in the sample stimulates the scintillating fluid, which then produces photons. These photons are then detected in the photomultiplier tubes 53. The counts produced by photomultiplier tubes 53 may be displayed in a table or graphically, to indicate the number of counts occurring over a period of time. In a known manner these characteristics can indicate the amount of radioactivity in components of the sample under test.

After the test is completed, sample cell 16 can be replaced by moving the cell assembly. Specifically, controller 105 will command stepper motor 96 to advance a predetermined number of increments. This shaft revolution will cause drive arm 102 to move to the right, thereby extending rods 60 and 58. Consequently, yoke plate 62 will extend beyond wall W, ultimately bringing cell 17 in registry with the photomultiplier tubes as illustrated in FIG. 4. As the yoke plate 62 extends, bellows 94 expands to keep light from leaking through the yoke plate 62 and the opening 46 of chamber 44.

After sample cell 16 is replaced by sample cell 17, the characteristics of the measurement will change accordingly. In instances where sample cell 17 is smaller, resolution and dynamic range will increase, while sensitivity decreases. This change can be important where closely spaced, high activity peaks are expected. Alternatively, sample cell 17 may have a larger volume, which then increases sensitivity to facilitate detection of low activity peaks.

Also, the substitution may change the scintillator method from a solid packed scintillator to an injected liquid scintillator. Accordingly, the detection characteristics will change and facilitate detection of different types of radiation. Likewise, a Cerenkov cell can be moved in or out of position to likewise change cell characteristics.

Importantly, the successive measurements are performed without the need to disconnect high pressure lines from fittings 20 through 23. Furthermore, these fittings move only a small amount. This makes the operation rather simple and avoids the possibility of leaking that could be caused by disconnecting the fittings 20 through 23 in order to replace cell block 12 or 15 with an alternate cell body or a separate sealed standard.

The controller 105 can also be preprogrammed as a scheduling means for moving the cell assembly to switch automatically between cells 16 and 17 on a predetermined schedule. This preprogramming can anticipate the characteristics of successive samples that may be encountered on different runs.

The term "run" is defined as the measurement of a discrete sample from a single origin, such as a single vial, to obtain consistent or correlated sample data. Thus, in a new "run" a sample may be drawn from a different vial or other source and can constitute a totally different result having unrelated characteristics and constituents.

In certain advanced embodiments, controller 105 can be programmed to change sample cells during the course of an individual run. For example, an operator may anticipate that the eluate may have closely spaced, high activity peaks, followed by sparser, low activity peaks. In this hypothetical case, the system will start with a relatively small sample cell that has good resolution and dynamic range. After a preprogrammed amount of time has elapsed, controller 105 can actuate stepper motor 96 to move the cell assembly and bring a larger sample cell in position between the photomultiplier tubes in expectation of less active, sparser peaks. Besides volume changes, the cell type may be changed in certain embodiments, for example, from a packed cell to a liquid scintillator, or to a Cerenkov cell (or vice versa).

In automated embodiments, the switching valve 114 (FIG. 5) may be solenoid operated, and controlled by controller 105 (FIG. 3), so that the appropriate one of the cells 16 or 17 is automatically supplied with eluate (and/or liquid scintillator) as the cell is moved into the active position between the photomultiplier tubes.

At some time, the system may execute a self-calibration in response to a manual command or a preprogrammed calibration schedule. At that time cell bodies 12 and 15 will move beyond the photomultiplier tubes. Consequently, shutter 84 will be driven by spring 88 against the shutter stops 106. By positioning the standard block 26 (FIG. 1) inside shutter 84 (FIG. 3), one of the sealed standards 32 can be aligned with shutter slit 86. Thus light from only one sealed standard illuminates the photomultiplier tubes. The sealed standard produces a known amount of illumination. Therefore, the photomultiplier tubes can be calibrated to indicate an output in accordance with this known standard.

The controller 105 can now index stepper motor 96 a predetermined amount to bring another sealed standard 32 in alignment with shutter slit 86. This next sealed standard, if part of a count rate linearity series, will exhibit a different count rate. Should it be part of a series employed to test instrument response to quenching or a part of a series of different isotopes, either of which constitutes an alternative use, then it will exhibit a different apparent energy distribution, i.e., more or fewer photons will be produced on average for each reported decay event.

After a measurement or calibration is completed, the controller 105 (FIGS. 3 and 4) commands the stepper motor 96 to rotate and drive arm 102 inwardly. The home position of the stepping motor can be established at the end of each cycle by overdriving the motor until drive arm 102 comes against mechanical stop 104. This retracts rods 58 and 60 thereby retracting yoke plate 62. Consequently, cell bodies 12 and 15 retract and the bellows 94 collapses to the position shown in FIG. 3. Thereafter, cell 16 may be used in the manner first described herein.

In some embodiments, more than two sample cells may be used. In that case, additional fittings and sample lines will be employed in the cell assembly.

Moreover, in some embodiments the sample cells may be connected together in series inside the cell assembly itself, without the need to have external connections through fittings on the faceplate 18. In still other embodiments, the return lines of the two cells 16 and 17 may be connected together inside the cell assembly without the need for connecting them separately through fittings on the faceplate. In still other embodiments the cell assembly may have a two dimensional matrix of cells, in which case the cell assembly can be moved in two dimensions by an appropriate x-y translation mechanism.

It is to be appreciated that various other modifications may be implemented with respect to the above described preferred embodiments. For example, the light-tight sample chamber can have different shapes other than rectangular. Furthermore, instead of bellows, a light-tight telescopic fitting can be used. Also, while a yoke plate is shown mounted on sliding cylindrical rods, in other embodiments different types of moving linkages may be used instead. Moreover, the various mounting structures and drive mechanisms can be reconfigured depending upon the desired structural rigidity, strength, speed, temperature stability, capacity, etc.

Obviously, many modifications and variations of the present invention are possible in light of the above teachings. It is therefore to be understood that within the scope of the appended claims, the invention may be practiced otherwise than as specifically described.

We claim:

1. A continuous sample detector comprising:

a sample chamber;

a cell assembly having a spaced pair of sample cells, said cells being different, said cells each being mounted in said sample chamber and being adapted to conduct a continuous sample flow;

a sensor mounted and arranged proximate said cell assembly; and motion means for allowing relative motion between said sensor and said cell assembly to enable said sensor to alternately detect radiance predominantly from a selected one of said cells, said motion means being operable to bring together for interaction said sensor and a selected one of said cells at a position in said sample chamber that inhibits radiance originating from outside said selected one of said cells from reaching said sensor.

2. A continuous sample detector according to claim 1 wherein said sample cells have different volumes.

3. A continuous sample detector according to claim 1 wherein said sample cells each have a response that varies differently to accommodate variations in characteristics of radiance from said sample cells.

4. A continuous sample detector according to claim 3 wherein one of said sample cells favors detection of beta radiation.

5. A continuous sample detector according to claim 3 wherein one of said sample cells favors detection of soft gamma radiation.

6. A continuous sample detector according to claims 5 wherein another one of said sample cells is more suited to counting beta radiation than soft gamma radiation.

7. A continuous sample detector according to claim 3 wherein at least one of said sample cells is suitable for measurement of Cerenkov radiation.

8. A continuous sample detector according to claim 3 wherein only one of said sample cells is packed with radiance responsive material.

9. A continuous sample detector according to claim 1 wherein at least one of said sample cells is adapted to receive liquid scintillator.

10. A continuous sample detector according to claim 9 comprising:

a mixing means coupled to supply at least one of said sample cells, and adapted to connect to (a) a source of liquid scintillator, and (b) a source of eluate.

11. A continuous sample detector according to claim 10 wherein said mixing means is coupled to supply only one of said sample cells.

12. A continuous sample detector according to claim 1 wherein said sample cells are connected in series.

13. A continuous sample detector according to claim 12 comprising:

a mixing means coupled to supply at least one of said sample cells, and adapted to connect to (a) a source of liquid scintillator, and (b) a source of eluate.

14. A continuous sample detector according to claim 1 comprising:

a switching means having a pair of outlets coupled to different corresponding ones of said sample cells and an inlet adapted to connect to a source of eluate.

15. A continuous sample detector according to claim 1 for detecting characteristics of eluate continuously delivered from a chromatography column during a predetermined time interval, said motion means comprising:

a scheduling means for switching the sample cells during said predetermined time interval to enable said sensor to detect radiance predominantly from a different one of said cells.

16. A continuous sample detector according to claim 15 wherein said scheduling means is operable to automatically switch the sample cells after a predetermined delay interval.

17. A continuous sample detector according to claim 15 wherein said scheduling means is operable to automatically switch the sample cells in order to change the sample cells, which exhibit a different responsiveness to a sample therein.

18. A continuous sample detector according to claim 15 wherein said scheduling means is operable to automatically switch the sample cells in order to obtain a response that varies differently with variations in characteristics of radiance from said sample cells.

19. A continuous sample detector according to claim 15 comprising:
a motion means for sliding said cell assembly in said sample chamber.

20. A continuous sample detector according to claim 1 wherein one of said sample cells is adapted to be removable from the other one of the sample cells.

21. A continuous sample detector according to claim 1 wherein one of said sample cells is adapted to be replaceable to change characteristics of said pair of sample cells.

22. A continuous sample detector according to claim 1 wherein said sample cells have a quick disconnect coupling for permitting replacement of one of said sample cells to change characteristics of said pair of sample cells.

23. A continuous sample detector according to claim 1 comprising:
standard source of radiance mounted adjacent to said cell assembly.

24. A continuous sample detector according to claim 23 wherein said standard source comprises:
a plurality of standards mounted and arranged proximate said cell assembly and said sensor to encounter relative reciprocation for allowing said sensor to alternately sense radiance predominantly from said cell assembly or predominantly from a selected one of said standards.

25. A continuous sample detector according to claim 23 wherein said standard source is attached to said cell assembly to move therewith relative to said sensor.

26. A continuous sample detector according to claim 23 comprising:
a shutter mounted to selectively stop radiance from said standard source.

27. A continuous sample detector according to claim 26 wherein said shutter is slidably mounted inside said sample chamber.

28. A continuous sample detector according to claim 26 wherein said standard source is attached to said cell assembly to move therewith relative to said sensor, said shutter being mounted to slide with said standard source and said cell assembly, said sample chamber including:
a shutter stop for stopping said shutter from moving and allowing said standard source to move relative to said shutter; and
a shutter spring for urging said shutter toward said cell assembly to cover said standard source.

29. A continuous sample detector according to claim 1 wherein said cell assembly is slidably mounted in said sample chamber to move relative to said sensor.

30. A continuous sample detector according to claim 1 wherein said sample chamber is light-tight.

31. A continuous sample detector according to claim 1 wherein said sample chamber is light-tight and has an opening, said cell assembly being at least partially mounted in said opening, said detector comprising:
a bellows mounted at said opening to stretch away from said cell chamber and encircle said cell assembly.

32. A continuous sample detector according to claim 1 wherein said sample chamber is light-tight, and wherein said sensor comprises at least one light sensitive transducer.

33. A continuous sample detector according to claim 1 wherein said sample chamber is light-tight, and wherein said sensor comprises an opposing pair of photomultipliers.

34. A continuous sample detector according to claim 1 wherein said cell assembly comprises:
a faceplate for supporting said cell assembly in said sample chamber, said faceplate having four fittings communicating with said sample cells.

35. A continuous sample detector according to claim 1 wherein said sample cells each comprise:
radiance transparent tubing.

36. A continuous sample detector according to claim 35 wherein said tubing is wound into a coil.

37. A method employing a sensor for continuously detecting in a sample flow, radiance predominantly from one of a pair of sample cells within a common housing that are connected through a plurality of sample lines in a cell assembly, comprising the steps of:
positioning said sensor and said cells within said common housing to detect radiance with said sensor from predominantly a first one of said sample cells;
passing the sample flow through the first one of said sample cells; and
changing the relative position of said sensor and said sample cells within said common housing to detect radiance with said sensor from predominantly a second one of said sample cells; and
passing the sample flow through the second one of said sample cells, without substituting a different flow in said first one of said sample cells, and without disconnecting any of said plurality of sample lines.

38. A method according to claim 37 wherein the step of changing the relative position of the sensor and the cells is performed in a manner to change the sample cells, which exhibit a different responsiveness to a sample therein.

39. A method according to claim 37 wherein the step of changing the relative position of the sensor and the cells is performed in a manner to change the sample cells, which exhibit a different responsiveness to varying radiance characteristics from a sample therein.

40. A method according to claim 37 wherein before the passing of the sample flow through one of said sample cells, liquid scintillator is first mixed with said sample flow.

41. A method according to claim 37 wherein the sample flow passing through the first one of the sample cells is then entirely passed through the second one of the sample cells.

42. A method according to claim 37 comprising the step of:
diverting the sample flow from the first one of said sample cells to said second one of said sample cells.

43. A method according to claim 37 comprising the step of:
chromatographically partitioning said sample flow before delivery to said sample cells; and
delivering the chromatographically partitioned sample flow continuously during a predetermined time interval.

44. A method according to claim 43 wherein the step of changing the relative position of the sensor and the sample cells is performed during said predetermined time interval.

45. A method according to claim 37 employing a standard source of radiance, comprising the step of:

calibrating said sensor within said common housing by separating said sensor and said sample cells and disposing said sensor and said standard source within said common housing to detect with said sensor, radiance predominantly from said standard source, without disconnecting any of the plurality of sample lines.

46. A method according to claim 45 wherein the step of calibrating said sensor is performed by:

simultaneously moving said cell assembly and said standard source together relative to said sensor.

47. A method according to claim 45 wherein said step of calibrating employs a shutter and is performed by:

relatively adjusting said shutter and said standard source to release radiance from said standard source.

48. A method according to claim 45 comprising the step of:

chromatographically partitioning said sample flow before delivery to said sample cells.

* * * * *